United States Patent [19]

Roth et al.

[11] Patent Number: 4,992,561

[45] Date of Patent: Feb. 12, 1991

[54] SIMPLE CONVERSION OF ARTEMISINIC ACID INTO ARTEMISININ

[75] Inventors: Ronald J. Roth; Nancy A. Roth, both of Fairfax

[73] Assignee: The United States of America as represented by the Secretary of the Army, Washington, D.C.

[21] Appl. No.: 521,958

[22] Filed: May 11, 1990

[51] Int. Cl.$^5$ ............................................. C07D 493/18
[52] U.S. Cl. ................................ 549/279; 204/157.69
[58] Field of Search .................... 549/279; 204/157.69

[56] References Cited

PUBLICATIONS

Xu. CA 99: 158654V.

*Primary Examiner*—Jane T. Fan
*Attorney, Agent, or Firm*—Anthony T. Lane; Werten F. W. Bellamy; Gary L. Hausken

[57] ABSTRACT

This invention relates to a novel process for producing artemisinin from artemisinic acid. The artemisinic acid is reduced to dihydroartemisinic acid by reduction of the exocyclic methylene group. The dihydroartemisinic acid is then oxidized in two successive steps to form artemisinin.

8 Claims, No Drawings

SIMPLE CONVERSION OF ARTEMISINIC ACID INTO ARTEMISININ

GOVERNMENT INTEREST

The invention described herein may be manufactured, licensed and used by or for govermental purposes without the payment of any royalties to us thereon.

BACKGROUND OF THE INVENTION

The photooxidation of artemisinic (arteannuic) acid (Compound 1), has been studied by several groups in a search for a route from this relatively abundant constituent of the plant *Artemisia annua* to the antimalarial drug artemisinin (qinghaosu) (Compound 3) which is present in the same plant in very low concentration.

Because there is far more artemisinic acid (Compound 1) than artemisinin (Compound 3) in *Artemisia annua*, the conversion of the former to the latter has received a great deal of attention. Prior synthetic conversion of 1 to 3 required a greater number of steps, produced a yield of approximately 7% and required the use of column chromatography for purification of the resulting artemisinin. Other attempts to simplify the process resulted in conversion of artemisinic acid into desoxyartemisinin, but did not . result in conversion to artemisinin.

The novel process described herein provides increased yields of artemisinin by photooxidation of dihydroartemisinic acid (Compound 2) in a simple procedure which does not require column chromatography. Because artemisinic acid can be easily isolated from *Artemisia annua* and purified without recourse to column chromatography, the process disclosed herein provides a simpler, less costly, and more efficient process for producing artemisinin. Furthermore, the novel process can more than double production of artemisinin from the plant material by utilization of artemisinic acid, which was previously discarded.

Another advantage of this process is that it provides a short route for deuterium-labelled artemisinin.

SUMMARY OF THE INVENTION

Artemisinic acid (Compound 1), which has been isolated from *Artemisia annua* and purified, is converted to dihydroartemisinic acid (Compound 2) by reduction of the exocyclic methylene group. In a two step procedure the dihydroartemisinic acid (Compound 2) is first photooxidized, destroying the starting material. Allowing the crude photolysis mixture to stand at room temperature resulted in a remarkable transformation into artemisinin (Compound 3).

DETAILED DESCRIPTION OF THE INVENTION

Artemisinic acid is reduced to dihydroartemisinic acid by reduction of the exocyclic methylene group. Artemisinic acid and nickel chloride, or nickel chloride hexahydrate, are dissolved in methanol, and excess lithium borohydride or sodium borohydride is added in portions until all the artemisinic acid has been consumed. Where deuterium-labelled artemisinin is desired, a deuterated borohydride is substituted for its protium analog. After acidification with aqueous hydrochloric acid, extraction with diethyl ether, and crystallization from acetonitrile, dihydroartemisinic acid is obtained.

The dihydroartemisinic acid is then mixed with an organic solvent and a photosensitizer. Two solvents, acetone and methylene chloride, have been found to be particularly suitable for this purpose. Methylene blue is an appropriate photosensitizer. Rose bengal or tetraphenylporphine may also be used as photosensitizers. Optimal yields were achieved with acetone when the temperature of the solvent was maintained near 0°, by use of an ice bath. With methylene chloride the greatest yield was achieved when the temperature of the solvent was maintained at −78°.

The dihydroartemisinic acid is then oxidized by irradiating the mixture with visible light while exposed to oxygen or air. Any visible light source, including sunlight, is capable of inducing the desired result. A high intensity light source, such as an electric discharge lamp, proved beneficial in laboratory tests.

After the oxidation is complete, the solvent is removed from the mixture by evaporation leaving a crude residue. The photosensitizer is removed by mixing this residue with diethyl ether and filtering off the insoluble sensitizer. The diethyl ether is then evaporated, leaving a colorless residue.

This residue is then mixed with a suitable organic solvent. Several solvents have been found well-suited for this purpose including: hydrocarbon solvents, such as petroleum ether, benzene, hexane and pentane, and halogenated solvents, such as methylene chloride, carbon tetrachloride, or a Freon. Freon is a trademark for a group of chemical compositions including but not limited to 1,1,2-trichloro-1,2,2-trifluoroethane (Freon 113), trichlorofluoromethane (Freon 11); dichlorodifluoromethane (Freon 12), tetrafluoromethane (Freon 14); 1,2,-dichloro-1,1,2,2-tetrafluoroethane (Freon 114); and octafluorocyclobutane (Freon C318). Petroleum ether afforded the cleanest product and relatively high yields. Although capable of producing the desired result, diethyl ether, acetonitrile and acetone were poor solvents, producing only small amounts (1-2%) of artemisinin. Trifluoroacetic acid may be added as a catalyst. The mixture is then allowed to stand until the formation of artemisinin is complete.

The solution is then separated from insoluble residue by decanting and the residue is further extracted with additional solvent. The combined solutions are concentrated to afford crude artemisinin which is purified by recrystallization.

WORKING EXAMPLES

The working examples set forth below illustrate the process using representative solvents and catalysts, but in no way limit the scope of the invention.

In each of the working examples artemisinic acid is isolated from *Artemisia annua* extract by simple aqueous sodium carbonate extraction and is purified. Artemisinic acid and nickel chloride hexahydrate were dissolved in methanol. An excess of sodium borohydride was added in portions until all the artemisinic acid was consumed. The solution was then acidified with aqueous hydrochloric acid. The dihydroartemisinic acid was isolated by extraction with diethyl ether followed by crystallization from acetonitrile.

EXAMPLE 1

A solution of dihydroartemisinic acid (500 mg) and methylene blue (5 mg) in acetone (80 ml) was cooled in ice. Oxygen was bubbled through the solution while irradiating with a high intensity electric discharge lamp. After 30-60 minutes, the solvent was removed, the residue taken up in diethyl ether, and the mixture filtered to remove the methylene blue.

The diethyl ether was evaporated and the residue mixed with petroleum ether (75 ml) and trifluoroacetic acid (3 drops). After standing 4-5 days, the petroleum ether solution was decanted and the residue was stirred in additional boiling petroleum ether. The combined petroleum ether extracts were concentrated to afford artemisinin which was recrystallized from cyclohexane in 28% yield. Flash chromatography of the mother liquors afforded a small additional amount of artemisinin.

EXAMPLE 2

The dihydroartemisinic acid (1.0 g) and methylene blue (6 mg) were dissolved in dichloromethane (80 ml). Oxygen was passed through the solution at −78° C. while irradiating with a high intensity electric discharge lamp. After 90 minutes, the solvent was evaporated at room temperature. The residue was taken up in diethyl ether and filtered to remove the methylene blue. Solvent was again removed and the residue mixed with 150 ml of petroleum ether.

After standing at room temperature for 4 days, the petroleum ether solution was decanted and the residue stirred with additional petroleum ether. The solvent was evaporated from the combined petroleum ether solutions. After redissolving the residue in diethyl ether, the solution was washed with 5% aqueous sodium carbonate (2×25 ml), water (1×25 ml), and brine (1×25 ml). The diethyl ether solution was dried with magnesium sulfate, solvent was removed, and the residue was mixed with petroleum ether (10 ml). Crude artemisinin (170 mg) was crystallized from solution. Recrystallization from cyclohexane afforded 142 mg of artemisinin. Flash chromatography of the mother liquors and the petroleum ether-insoluble fraction followed by recrystallization as above afforded an additional 56 mg of artemisinin for a total yield of 17%.

TABLE

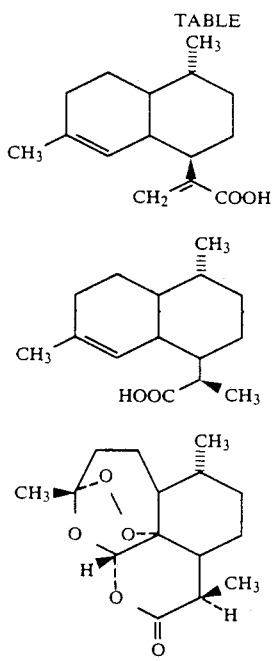

Compound 1

Compound 2

Compound 3

We claim:

1. A process for producing artemisinin from artemisinic acid comprising the steps of:
   (a) dissolving artemisinic acid and nickel chloride in methanol;
   (b) adding a borohydride selected from the group consisting essentially of sodium borohydride or lithium borohydride;
   (c) acidifying the solution;
   (d) isolating the dihydroartemisinic acid;
   (e) mixing the dihydroartemisinic acid and a photosensitizer in solution with a suitable organic solvent;
   (f) oxidizing the dihydroartemisinic acid in the presence of a visible light source;
   (g) evaporating the solvent, leaving a residue;
   (h) mixing the residue formed in step (g) with a suitable organic solvent;
   (i) air-oxidizing the mixture formed in step (h) for a suitable period; and
   (j) decanting the solution formed in step (i), and concentrating said solution to isolate artemisinin.

2. The process in accordance with claim 1, wherein:
   (a) the solvent in step (e) is acetone or methylene chloride, and
   (b) the solvent in step (h) is a hydrocarbon solvent or a halogenated solvent.

3. The process in accordance with claim 2 wherein the solvent in step (h) is selected from the group consisting essentially of petroleum ether, benzene, hexane, pentane, methylene chloride, carbon tetrachloride or a Freon.

4. The process in accordance with claim 3 wherein the solvent is 1,1,2-trichloro-1,2,2-trifluoroethane.

5. The process in accordance with claim 1, wherein the photosensitizer in step (f) is selected from the group consisting essentially of methylene blue, rose bengal or tetraphenylporphine.

6. The process in accordance with claim 1, wherein a catalytic amount of trifluoroacetic acid is added to the solution in step (i) and removed in step (j).

7. The process in accordance with claim 1 in which the light source in step (c) is a high intensity electric discharge lamp.

8. A process for producing artemisinin from artemisinic acid comprising the steps of:
   (a) dissolving artemisinic acid and nickel chloride hexahydrate in methanol;
   (b) adding sodium borohydride;
   (c) acidifying the solution with hydrochloric acid;
   (d) isolating the dihydroartemisinic acid by extraction with diethyl ether and crystallization from acetonitrile;
   (e) mixing the dihydroartemisinic acid in solution with acetone and a catalytic amount of methylene blue;
   (f) oxidizing the dihydroartemisinic acid in the presence of a high intensity electric discharge lamp;
   (g) evaporating the solvent, leaving a residue;
   (h) mixing the residue with diethyl ether, filtering to remove the methylene blue, and evaporating the diethyl ether to again leave a residue;
   (i) mixing the residue formed in step (h) with petroleum ether and a catalytic amount of trifluoroacetic acid;
   (j) air-oxidizing the mixture formed in step (i) for a suitable period; and
   (k) decanting and concentrating the solution, and purifying the residue to isolate artemisinin.

* * * * *